United States Patent
Itoh (10) Patent No.: US 9,889,453 B2
(45) Date of Patent: Feb. 13, 2018

(54) CENTRIFUGAL SEPARATION APPARATUS HAVING A PLURALITY OF SEPARATORS ARRANGED AND MOVEABLE IN A BASE AND CENTRIFUGAL SEPARATION METHOD

(71) Applicant: AOI SEIKI CO., LTD., Kumamoto-shi, Kumamoto-ken (JP)

(72) Inventor: Teruaki Itoh, Kumamoto (JP)

(73) Assignee: AOI SEIKI CO., LTD., Kumamoto (JP)

( * ) Notice: Subject to any disclaimer, the term of this patent is extended or adjusted under 35 U.S.C. 154(b) by 0 days.

(21) Appl. No.: 15/216,106

(22) Filed: Jul. 21, 2016

(65) Prior Publication Data

US 2017/0021367 A1   Jan. 26, 2017

(30) Foreign Application Priority Data

Jul. 24, 2015   (JP) .................... 2015-146753

(51) Int. Cl.
*B04B 5/10*   (2006.01)
*B04B 13/00*   (2006.01)
(Continued)

(52) U.S. Cl.
CPC .............. *B04B 5/10* (2013.01); *B04B 5/0407* (2013.01); *B04B 5/0414* (2013.01);
(Continued)

(58) Field of Classification Search
CPC ......... B04B 5/10; B04B 13/00; B04B 5/0407; B04B 9/00; B04B 5/0421; B04B 5/0414; B04B 2011/046; B04B 9/10; G01N 35/04; G01N 35/00; G01N 2035/0465; G01N 2035/00495; G01N 2035/0406
See application file for complete search history.

(56) References Cited

U.S. PATENT DOCUMENTS 5,721,676 A * 2/1998 Bolden ................. A61M 1/387
                                                     422/72
5,740,185 A * 4/1998 Bosse ................. G11B 20/1833
                                                     356/39
(Continued)

FOREIGN PATENT DOCUMENTS

CN       1894397         7/2011
EP     2 664 925         11/2013
(Continued)

OTHER PUBLICATIONS

Extended European Search Resort issued in App. No. 16180181.6 dated Nov. 25, 2016.
(Continued)

*Primary Examiner* — Charles Cooley
(74) *Attorney, Agent, or Firm* — Nixon & Vanderhye P.C.

(57) ABSTRACT

A centrifugal separation apparatus includes a plurality of centrifugal separators each comprising a rotator which supports a plurality of sample containers containing a sample therein, a base in which the centrifugal separators are arranged in columns and stages and a route is defined therein, the centrifugal separators being movable inside the base, and a movement mechanism that sequentially move the centrifugal separators along the route in the base.

3 Claims, 8 Drawing Sheets

(51) Int. Cl.
B04B 5/04 (2006.01)
B04B 9/00 (2006.01)
G01N 35/04 (2006.01)
B04B 11/04 (2006.01)
G01N 35/00 (2006.01)

(52) U.S. Cl.
CPC .............. B04B 5/0421 (2013.01); B04B 9/00 (2013.01); B04B 13/00 (2013.01); G01N 35/04 (2013.01); B04B 2011/046 (2013.01); G01N 2035/00495 (2013.01); G01N 2035/0406 (2013.01); G01N 2035/0465 (2013.01)

(56) References Cited

U.S. PATENT DOCUMENTS

| 8,795,144 | B2* | 8/2014 | Pedrazzini | B04B 5/0421 494/20 |
|---|---|---|---|---|
| 9,302,275 | B2* | 4/2016 | Verweij | B04B 5/10 |
| 2004/0089737 | A1* | 5/2004 | Itoh | B04B 5/0421 239/264 |
| 2004/0184959 | A1 | 9/2004 | Itoh | |
| 2007/0148764 | A1 | 6/2007 | Suzuki et al. | |
| 2011/0045958 | A1* | 2/2011 | Pedrazzini | B04B 5/0421 494/8 |
| 2015/0141232 | A1* | 5/2015 | Verweij | B04B 5/10 494/16 |
| 2015/0218618 | A1 | 8/2015 | Tajima et al. | |
| 2017/0021367 | A1* | 1/2017 | Itoh | B04B 5/0407 |
| 2017/0219616 | A1* | 8/2017 | Pedrazzini | G01N 35/00009 |

FOREIGN PATENT DOCUMENTS

| JP | 2004-151024 | 5/2004 |
|---|---|---|
| JP | 3675799 | 7/2005 |
| TW | M358011 | 6/2009 |
| TW | 201111026 | 4/2011 |
| TW | 201408781 | 3/2014 |
| TW | M505344 | 7/2015 |

OTHER PUBLICATIONS

Canadian Office Action issued in Appln. No. 2,937,000 dated Jun. 13, 2017.

Taiwanese Office Action issued in Appln. No. 105122610 dated Jul. 6, 2017 (w/ translation).

Korean Office Action issued in Appln. No. 10-2016-0092864 dated Nov. 16, 2017 (with translation).

\* cited by examiner

FIG. 8

CENTRIFUGAL SEPARATION APPARATUS HAVING A PLURALITY OF SEPARATORS ARRANGED AND MOVEABLE IN A BASE AND CENTRIFUGAL SEPARATION METHOD

CROSS-REFERENCE TO RELATED APPLICATION

This application is based upon and claims the benefit of priority from prior Japanese Patent Application No. 2015-146753, filed Jul. 24, 2015, the entire contents of which are incorporated herein by reference.

FIELD

The present invention relates to a centrifugal separation apparatus employing a plurality of centrifugal separators, and to a centrifugal separation method.

BACKGROUND

As a centrifugal separation apparatus for centrifugally separating a sample such as blood, the following type of apparatus is known in the art. The apparatus employs a plurality of buckets swingably attached to the circumference of a disk-like rotator. Sample containers holding a sample to be processed are fitted in the buckets, and the rotator is rotated at high speed for centrifugal separation processing. (Jpn. Pat. Appln. KOKAI Publication No. 2004-151024).

In the above apparatus, the sample containers are sequentially conveyed from a processing line, where the sample is subjected to biochemical analysis and various pre-processing, to the rotators of a plurality of centrifugal separators. When a predetermined number of sample containers have been conveyed, the rotators of the centrifugal separators are rotated for centrifugal separation processing. When the centrifugal separation processing has been performed for a predetermined time, the rotators are stopped, and the sample containers are sequentially taken out and returned to the processing line.

If the number of sample containers is large, the time required for conveying them to the rotators and returning them to the processing line is inevitably long. As a result, the efficiency of the centrifugal separation processing of the above-mentioned centrifugal separation apparatus decreases. Accordingly, an object of the present invention is to provide a centrifugal separation apparatus and a centrifugal separation method which ensure high processing efficiency.

The embodiment described herein enables enhancing the processing efficiency of centrifugal separation processing.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION

Figure 1:
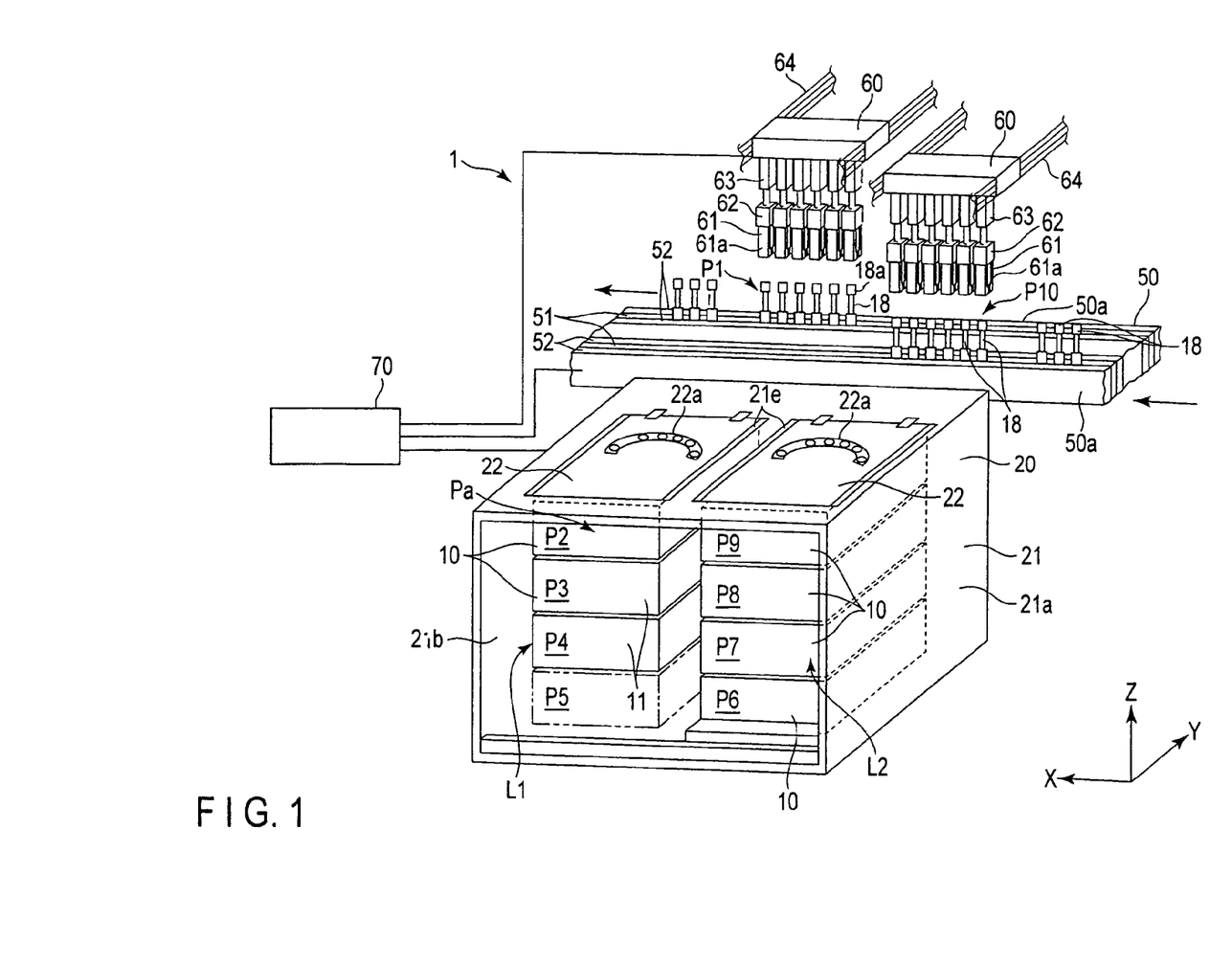
FIG. 1 is a perspective view of a centrifugal separation apparatus according to one embodiment of the present invention.
Figure 2:
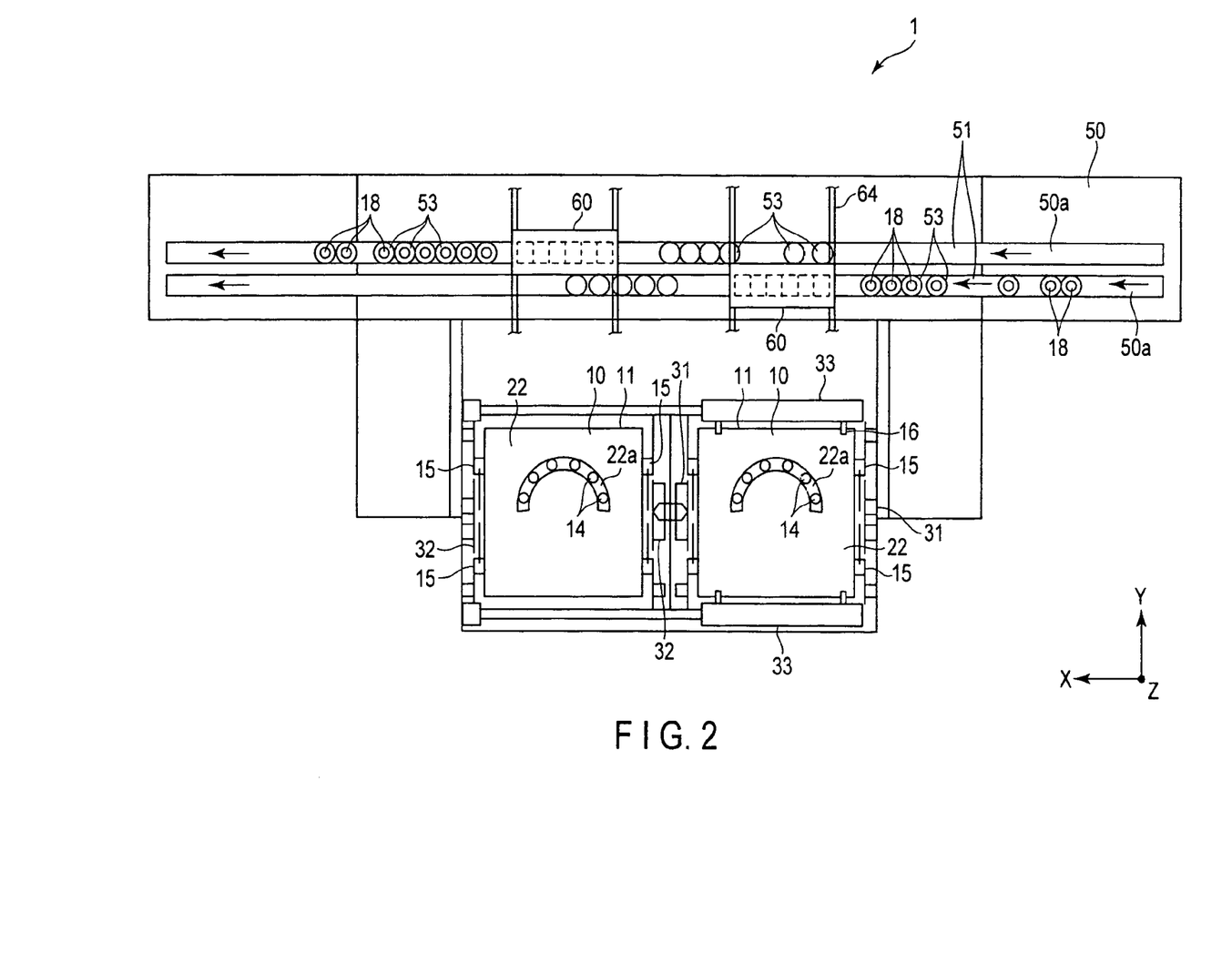
FIG. 2 is a plan view of the centrifugal separation apparatus.
Figure 3:
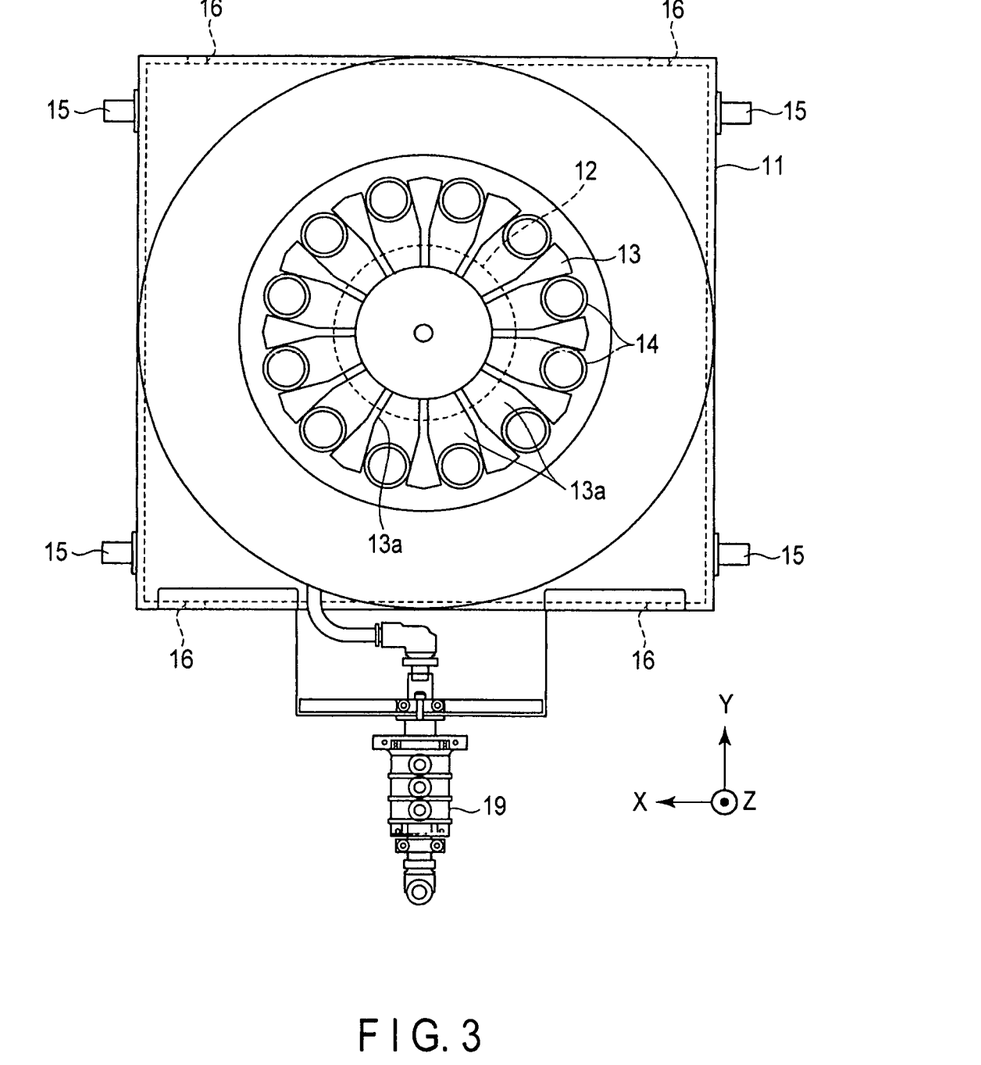
FIG. 3 is a plan view of a centrifugal separator of the centrifugal separation apparatus.
Figure 4:
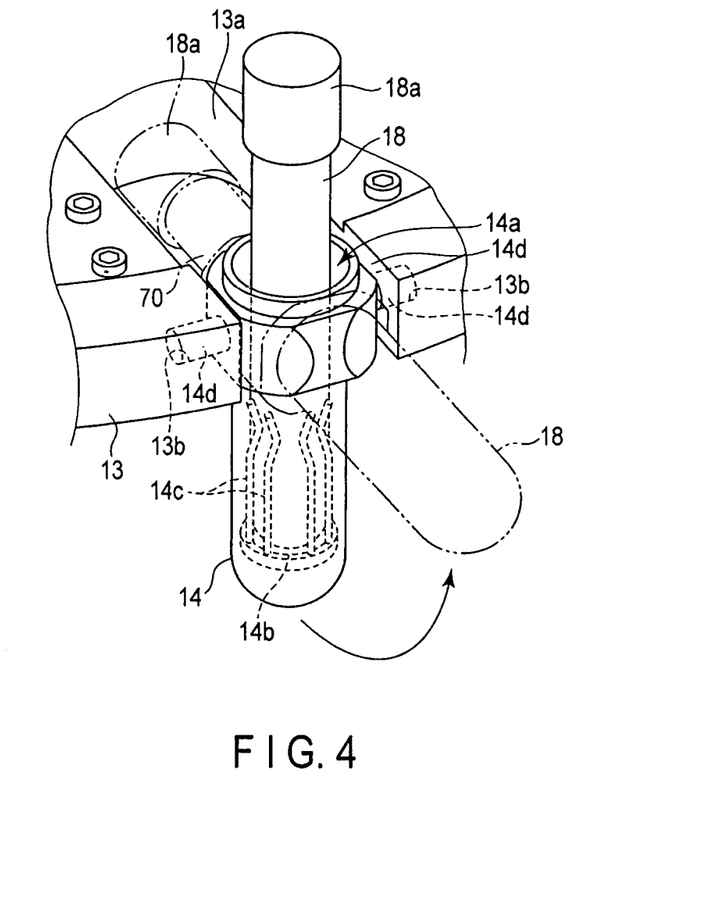
FIG. 4 is a perspective view showing part of the centrifugal separator.
Figure 5:
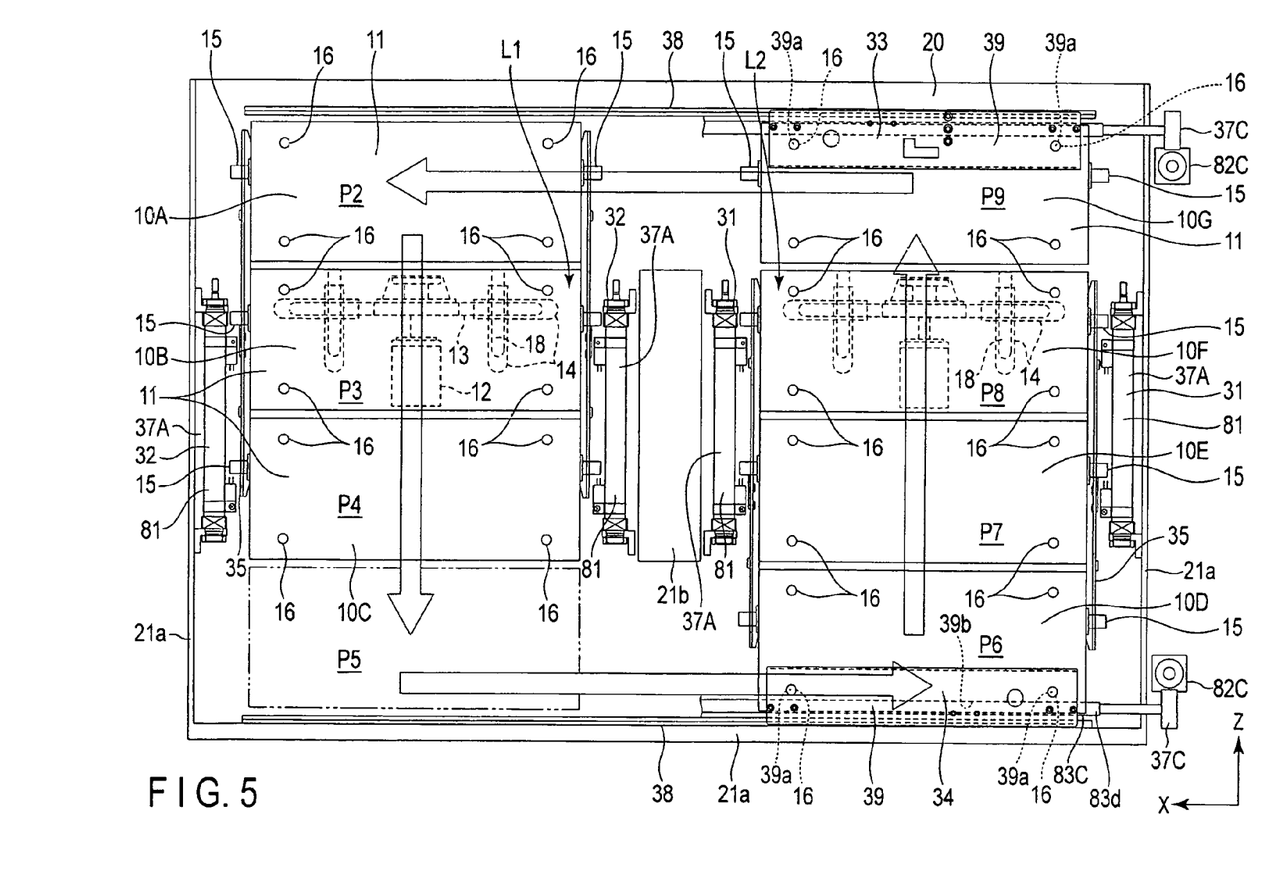
FIG. 5 is an explanatory diagram illustrating the movement mechanism of the centrifugal separation apparatus.
Figure 6:
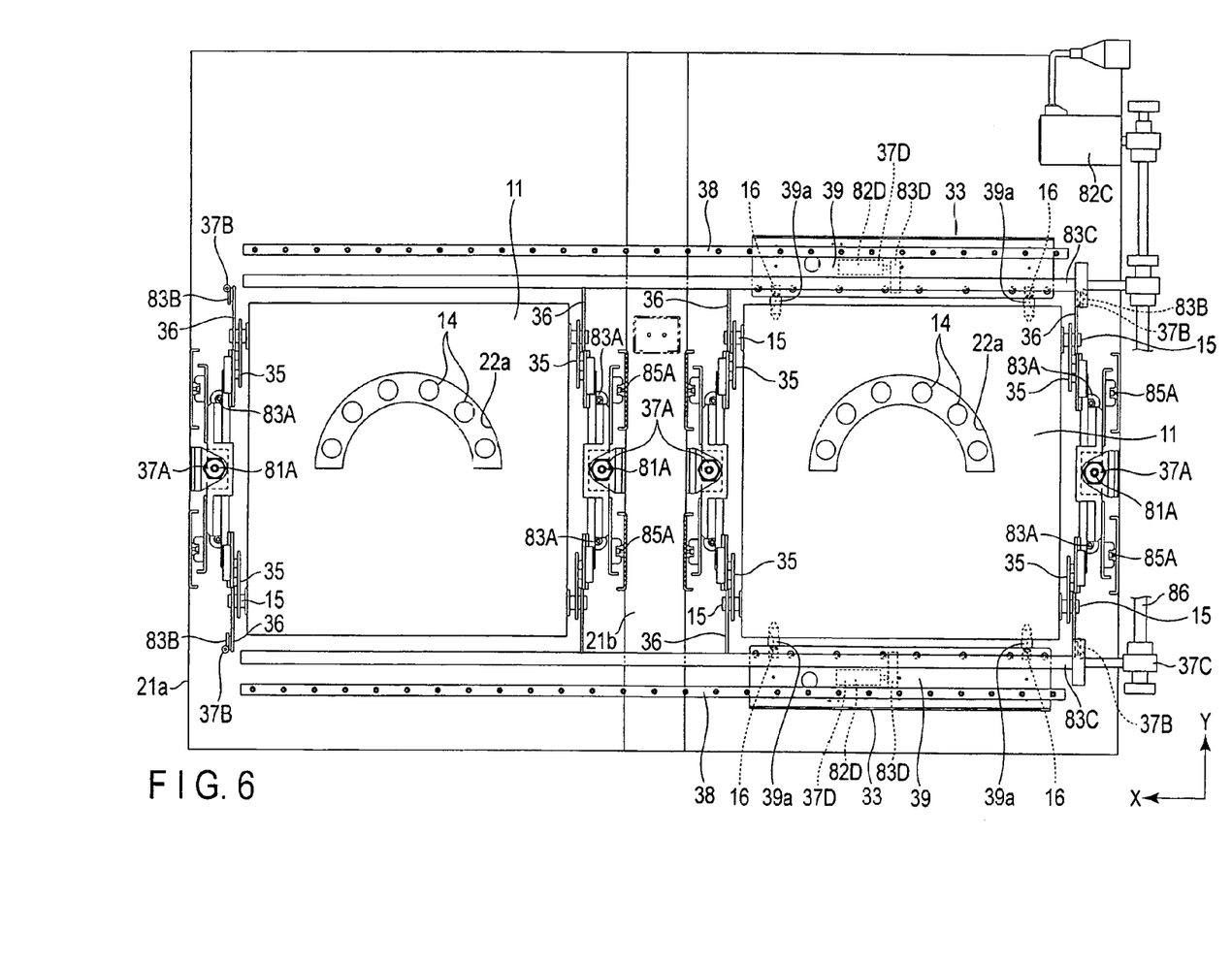
FIG. 6 is an explanatory diagram illustrating the movement mechanism of the centrifugal separation apparatus.

A centrifugal separation apparatus 1 according to one embodiment of the present invention will be described with reference to FIGS. 1 to 8. FIG. 1 is a schematic plan view of the centrifugal separation apparatus 1 of the first embodiment of the present invention, and FIG. 2 is a plan view illustrating the schematic structure of the centrifugal separation apparatus 1. FIG. 3 is a plan view illustrating the structure of a centrifugal separator 10, and FIG. 4 is a perspective view illustrating the support structure of a bucket 14 of the centrifugal separator 10. FIGS. 5 through 8 are explanatory diagrams illustrating the movement mechanism 30 of the centrifugal separation apparatus 1. FIG. 5 being a plan view, FIG. 6 being a front view, and FIGS. 7 and 8 being side views. For illustrative purposes, structures are illustrated on an enlarged or reduced scale, and illustration of part of the structures is omitted. In the Figures, arrows X, Y and Z indicate three directions perpendicular to one another. The X direction is the widthwise direction of the apparatus, the Y direction is the front-back direction thereof, and the Z direction is the vertical direction thereof.

As shown in FIGS. 1 and 2, the centrifugal separation apparatus 1 comprises: a plurality of centrifugal separators 10, a base 20 configured to contain the centrifugal separators 10; a movement mechanism 30 configured to sequentially move the centrifugal separators 10 along a predetermined route Pa inside the base 20; a conveyor line 50 provided on one side of the base 20; transfer mechanisms 60, one for taking in sample containers 10 to be subjected to centrifugal separation from the conveyor line 50 and conveying them into the base, and the other for taking out sample containers subjected to the centrifugal separation from the base 20 and conveying them to the conveyance line 50; and a controller 70 for controlling the centrifugal separators 10, the transfer mechanisms 60 and the movement mechanism 30.

As shown in FIGS. 1 through 4, each of the centrifugal separators 10 comprises a casing 11, a rotary motor 12 supported in the casing 11, a rotator 13 connected to the main shaft of the motor 12, and a plurality of buckets 14 swingably attached to the circumference of the rotator 13. The motors 12 of the centrifugal separators 10 are connected to a common power supply source 19.

The casing 11 is, for example, a rectangular box with an open top, and defines an inside space in which the motor 12 and the rotator 13 can be arranged.

Engagement projections 15, which are like columns protruding outward, are formed on the opposed X-direction end faces of the casing 11. The engagement projections 15 are located at the two Y-direction ends of each of the opposed side walls. The engagement projections 15 are insertable into hooks 35a and 36a of a movement frame 35 and a holding frame 36, which are to be described later, and are engageable with an elevating frame and the holding frame 36.

Engagement holes 16 depressed in the Y direction are formed in the Y-direction end faces of the casing 11. The engagement holes 16 are formed in such a manner that the engagement pins 39a of an upper slide mechanism 33 and a lower slide mechanism 34 can be inserted therein. The engagement holes 16 are engageable with a slider 39, described later.

The motor 12 is fixed to the bottom of the casing 11. The motor 12 comprises a main shaft extending upward in the Z direction, and the rotator 13 is connected to the main shaft.

The rotator 13 is arranged on the motor 12, and is connected to the main shaft of the motor 12, thereby enabling the rotator 13 to rotate. A plurality of slits 13a are radially formed in the circumference of the rotator 13. The slits 13a are open outward in the radial directions. In the present embodiment, the rotator 13 has twelve slits 13a, and twelve buckets 14 are swingably supported in the slits 13a.

Pivot support holes 13b are provided in the inner walls facing the outer circumference of the rotator 13, with the slit 13a interposed. A pair of shaft pins 14d extending from the opposed portions of the bucket 14 are supported by means of the pivot support holes 13b. The shaft pins 14d of the bucket 14 are inserted into the pivot support holes 13b, and the bucket 14 is fitted in the slit 13a in a swingable manner. By the centrifugal force caused by the rotation of the rotator 13, the bottom of the bucket 14 swings up outwardly. The bucket 14 is configured such that the axis of the bucket 14 can be made horizontal.

The bucket 14 is a cylindrical aluminum tube. It has an open top, defines a columnar insertion space 14a inside, and has a bottom. A sample container 18 can be inserted into the insertion space 14a of the bucket 14. A holding mechanism 14b for holding a test tube is provided in the insertion space 14a. The holding mechanism 14b is provided with a plurality of holding pins 14c which are elastically deformable in the radial direction. By the elastic force of the holding pins 14c, the outer surface of a test tube are held. A pair of shaft pins 14d are provided on the outer circumference of the upper portion of the bucket 14. The shaft pins 14d protrude outward. With the shaft pins 14d inserted into the pivot support holes 13b, a sample holder 53 is swingably held by the rotator 13.

The sample container 18 is, for example, a test tube, such as a vacuum blood-collecting tube in which blood or blood serum can be contained as a sample. The sample container 18 is cylindrical and has a bottom. A removable cap 18a is attached to the open top of the sample container 18. A label on which various kinds of data are printed as a bar code or letters is pasted to the side portion of the sample container 18.

As shown in FIGS. 1 through 8, the base 20 is provided with a box-like case 21 having openings formed in the top wall, and with lids 22 for covering the openings of the top wall of the case 21. The case 21 is a rectangular case including a plurality of wall members 21a, constituting side walls and a bottom wall, and frame members 21b. The case 21 defines a predetermined route Pa inside.

Route Pa is determined such that centrifugal separators 10 in different columns and different stages can be arranged. Route Pa starts at a take-in position P2 from which a sample container 18 is taken in and ends at a take-out position P9 from which the sample container 18 is taken out. In the present embodiment, two columns are defined in the X direction, and four stages are defined in the Z direction, and the case 21 accommodates a total of eight centrifugal separators 10. At all times, seven centrifugal separators 10 are arranged inside the case 21, with the area for one centrifugal separator being empty.

Route Pa includes an ascending column and a descending column which are juxtaposed in the X direction and in each of which centrifugal separators 10 are arranged in the Z direction. The uppermost stage of the descending column is a take-in position P2, and the uppermost stage of the ascending column is a take-out position P9.

The top plate of the case 21 has two upper openings 21e juxtaposed in the X direction. The upper openings 21e are located at positions corresponding to the take-in position P2 and the take-out position P9. The lids 22 are provided to open or close the upper openings 21e.

The lids 22 are located above the centrifugal separator 10 at the take-in position P2 and the centrifugal separator 10 at the take-out position P9, respectively. A take-in opening 22a and a take-out opening 22a, which are shaped like an arch corresponding to the shape of the sample container 18 and the bucket 14, are formed in the lids 22. Through the openings 22a, container hands 61 can be advanced into the base from above the lids 22. At the time of take-in or take-out operation, the buckets 14 of the centrifugal separators 10 inside the base 20 can be accessed by the container hands 61.

The movement mechanism 30 includes an elevating mechanism 31 for sequentially elevating the centrifugal separators 10 in the ascending column, a lowering mechanism 32 for sequentially lowering the centrifugal separators 10 in the descending column, an upper slide mechanism for sliding a centrifugal separator 10 from the uppermost stage of the ascending column to the uppermost stage of the descending column, and a lower slide mechanism for sliding a centrifugal separator 10 from the lowermost stage of the descending column to the lowermost stage of the ascending column.

The elevating mechanism 31 is provided with a plurality of movement frames 35 which are opposed to the X-direction end faces of the centrifugal separators in the ascending column, a plurality of holding frames 36 which are arranged on the opposite side of the movement frames 35, with the engagement projections interposed, a driving mechanism 37A for moving the movement frames 35 back and forth in the Y direction and Z direction, and a driving mechanism 37B for moving the holding frames 36 back and forth in the Y direction.

The lowing mechanism 32 is provided with a plurality of movement frames 35 which are opposed to the X-direction end faces of the centrifugal separators in the descending column a plurality of holding frames 36 which are arranged on the opposite side of the movement frames 35, with the engagement projections interposed, a driving mechanism 37A for moving the movement frames 35 back and forth in the Y direction and Z direction, and a driving mechanism 37B for moving the holding frames 36 back and forth in the Y direction.

Each of the movement frames 35 is a plate-like member arranged on one side of the paired engagement projections 15 of the casing 11 and having a plurality of hooks 35a on one edge thereof. The hooks 35a are recesses formed in the one edge and can be engaged with or disengaged from the engagement projections 15 when the movement frames 35 are advanced or retreated with reference to the engagement projections 15.

In the Z direction, the movement frames 35 have a length corresponding to three centrifugal separators, and three hooks 35a are juxtaposed in the Z direction.

The hooks 35a are provided in correspondence to how the centrifugal separators 10 are arranged along route Pa. To be more specific, the hooks 35a are arranged at the same pitch as the engagement projections 15.

The moving distance by which the movement frames 35 are elevated or lowered in the Z direction is determined based on the pitch of the engagement projections 15.

The moving distance by which the movement frames 35 are elevated or lowered in the Y direction is determined based on the insertion depth of the engagement projections 15 in the Y direction. To be more specific, when the movement frames 35 are advanced in the Y direction with reference to the engagement projections 15, the hooks 35a engage with the engagement projections 15. When the movement frames 35 are retreated in the Y direction, the hooks 35a disengage from the engagement projections 15.

Each of the holding frames 36 is a plate-like member arranged on the other side of the paired engagement projections 15 of the casing 11 and having a plurality of hooks 35a in one edge thereof. The hooks 35a are recesses formed on the one edge and can be engaged with or disengaged from the engagement projections 15 when the holding frames 36 are advanced or retreated with reference to the engagement projections 15.

In the Z direction, the holding frames 36 have a length corresponding to two centrifugal separators, and two hooks 35a are arranged in the Z direction.

The hooks 35a are provided in correspondence to how the centrifugal separators 10 are arranged along route Pa. To be more specific, the hooks 35a are arranged at the same pitch as the engagement projections 15.

The moving distance by which the holding frames 36 are elevated or lowered in the Z direction is determined based on the pitch of the engagement projections 15.

The moving distance by which the holding frames 36 are elevated or lowered in the Y direction is determined based on the insertion depth of the engagement projections 15 in the Y direction. To be more specific, when the holding frames 36 are advanced in the Y direction, the hooks 35a engage with the engagement projections 15. When the holding frames 36 are retreated in the Y direction, the hooks 35a disengage from the engagement projections 15.

Driving mechanism 37A comprises a vertically-movable cylinder 81A fixed to the case 21 by means of a guide rail mechanism 85A, a rotary motor 82A attached to the cylinder shaft of the vertically-movable cylinder 81A by means of a link member, a rack-and-pinion type driving force transmission mechanism 83A which converts the rotation of the output shaft of the rotary motor 82 into a reciprocating motion in the Y direction and transmits the reciprocating motion to the movement frames 35, and a plurality of guide mechanisms 84A for guiding the movement frames 35. Driving mechanism 37A permits the movement frames 35 to be supported by the case 21 to be movable in both the Z direction and the Y direction.

Driving mechanism 37B comprises a rotary motor 82B fixed to the case 21, a driving force transmission mechanism 83B which converts the rotation of the rotary motor 82B into a reciprocating motion in the Y direction and transmits the reciprocating motion to the holding frames 36, and a guide mechanism 84B for guiding the holding frames 36. Driving mechanism 37B permits the holding frames 36 to be supported by the case 21 to be movable in the Y direction.

Each of the driving force transmission mechanisms 83A and 83B is, for example, a rack-and-pinion type transmission mechanism comprising a pinion gear connected to the rotary motor 82 and rotated thereby and a rack gear engaged with the pinion gear. The guide mechanisms 84A and 84B are, for example, rail mechanisms comprising guide rails extending in guide directions.

Each of the upper slide mechanism 33 and the lower slide mechanism 34 comprises: a pair of guide rails 38 formed on the case 21; a plurality of sliders 39 engaged with the guide rails 38 and moving back and forth while being guided by the guide rails 38; driving mechanism 37C that moves the sliders 39 back and forth in the X direction; engagement pins 39a provided on each slider 39; and driving mechanism 37D that moves the engagement pins 39a in the Y direction relative to the sliders 39.

Each guide rail 38 extends in the X direction between the front and rear end portions of the base 20 and is located between the side walls of the base 20. Each guide rail 38 guides the sliders 39 in the X direction. The sliders 39 are engaged with the guide rails 38 and are supported thereby to be movable. The engagement pins 39a are provided on the Y-direction inward portions of the sliders 39 and are projected inward in the Y direction.

Driving mechanism 37C comprises a rotary motor 82C fixed to the case 21 and capable of rotating in two opposite directions, and a driving force transmission mechanism 83C which converts the rotation of the output shaft of the rotary motor 82C into a reciprocating motion in the X direction and transmits the reciprocating motion to the sliders 39.

The driving force transmission mechanism 83C is, for example, a screw type transmission mechanism including (i) a screw shaft 83d having a spiral thread groove formed in the outer circumferential wall thereof and connected to the rotating shaft of the rotary motor 82C and (ii) screw holes 39b formed in the sliders 39 and having thread groove engaged with the screw shaft 38d. When the screw shaft 83d rotates in accordance with the rotation of the rotary motor 82C, the sliders 39 move in the X direction.

Driving mechanism 37D comprises a rotary motor 82D fixed to the sliders 39, and a rack-and-pinion type driving force transmission mechanism 83D which converts the rotation of the output shaft of the rotary motor 82D into a reciprocating motion in the Y direction and transmits the reciprocating motion to the engagement pins 39a.

In accordance with the rotations of the rotary motor 82 in the two directions, the engagement pins 39a advance or retreat between a hold position where the engagement pins 39a are inserted into the engagement holes 16 of the casing 11 and hold the casing 11 and a retreat position where the engagement pins 39a are pulled off the engagement holes 16 of the casing 11 and release the casing 11 from the held state.

The upper slide mechanism 33 is provided at each of the Y-direction end portions of the top portion of the apparatus. The lower slide mechanism 34 is provided at each of the Y-direction end portions of the bottom portion of the apparatus.

Each of the take-in and take-out transfer mechanisms 60 shown in FIGS. 1 and 2 comprises: a plurality of container hands 61 including opening/closing claws 61a capable of simultaneously holding adjacent sample-contained sample containers 18 (six containers in the present embodiment) and cylinder mechanisms 62 for opening or closing the claws 61a; cylinder mechanisms 63 which vertically move the container hands 61; and an electrically-operated belt conveyance mechanism 64 which moves hand units (each made up of container hand 61 and cylinder mechanism 63) back and forth in the Y direction by a predetermined distance.

The conveyance line 50 is a processing line for executing biochemical analysis and pre-processing for samples and is located, for example, on one side of the base 20. The conveyance line 50 comprises, for example, belt conveyors 51 and guide rails 52, both extending along two conveyance lanes 50a. Sample holders 53 for holding sample containers 18 in the upright state are set on each conveyance lane 50a and are sequentially moved. Each sample holder 53 comprises, for example, a holder base having a cylindrical insertion space inside, and the cylindrical insertion space is configured to receive a sample container 18. Like a bucket 14, a holding mechanism for holding a test tube is provided in the insertion space. The holding mechanism is provided with a plurality of elastically-deformable upright holding pins which are arranged annularly. By the elastic force of the holding pins, the outer surface of a test tube are held.

The controller 70 is connected to the detectors of the centrifugal separation apparatus 1. It is also connected to the motor 12, driving mechanisms 37A to 37D and belt conveyance mechanism 64. The controller 70 drives the motor 12, driving mechanisms 37A to 37D and belt conveyance mechanism 64 in accordance with the detection data detected at the detectors and various data and predetermined programs stored in a storage.

In the centrifugal separation apparatus 1 described above, the centrifugal separators 10, the movement mechanism 30, the driving elements of the transfer mechanisms 60, including motors 12 and driving mechanisms 37A to 37D, and various types of mechanisms such as belt conveyance mechanism 64, are connected to the controller 70 and operate at predetermined timings under the control of the controller 70.

Figure 7:
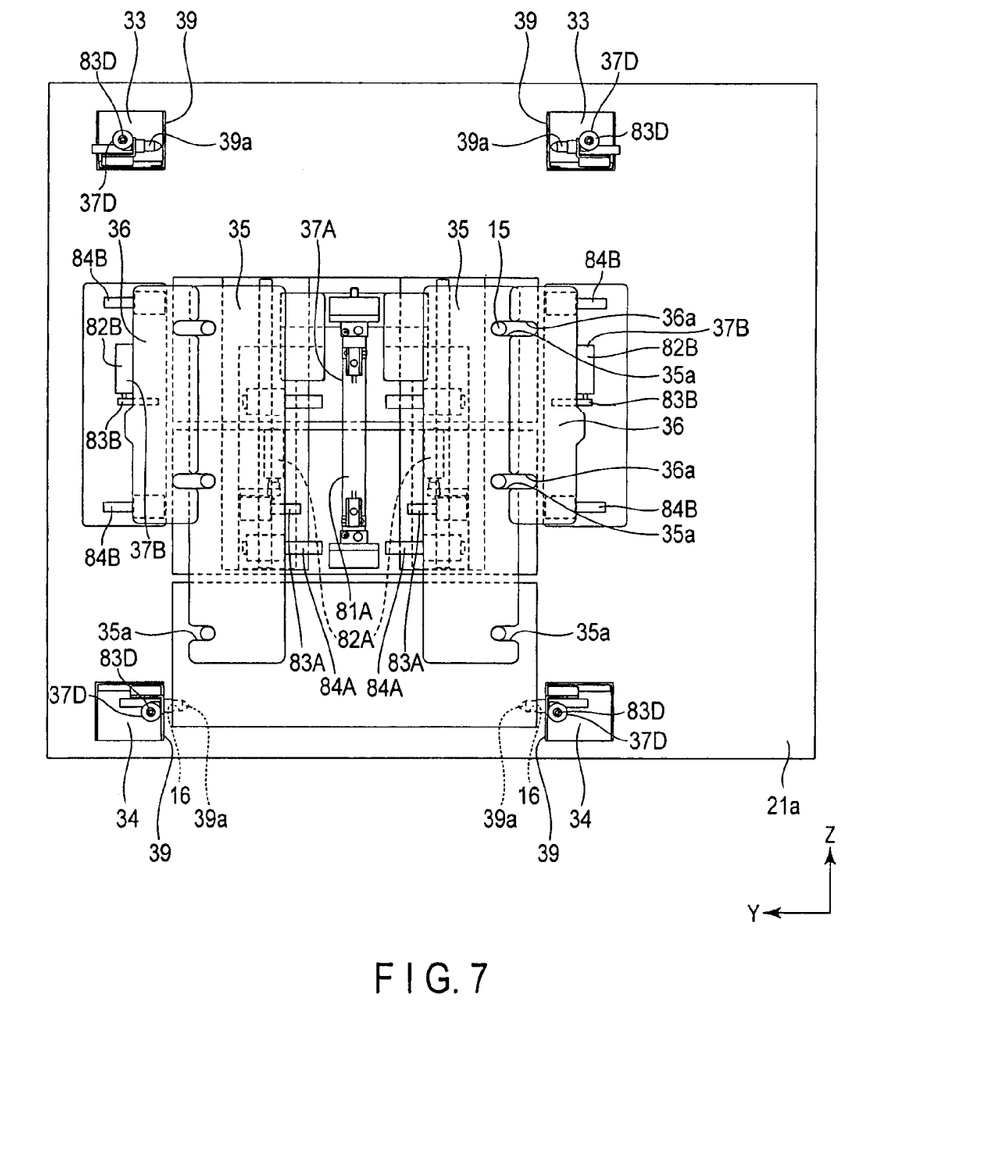
FIG. 7 is an explanatory diagram illustrating the movement mechanism of the centrifugal separation apparatus.
Figure 8:
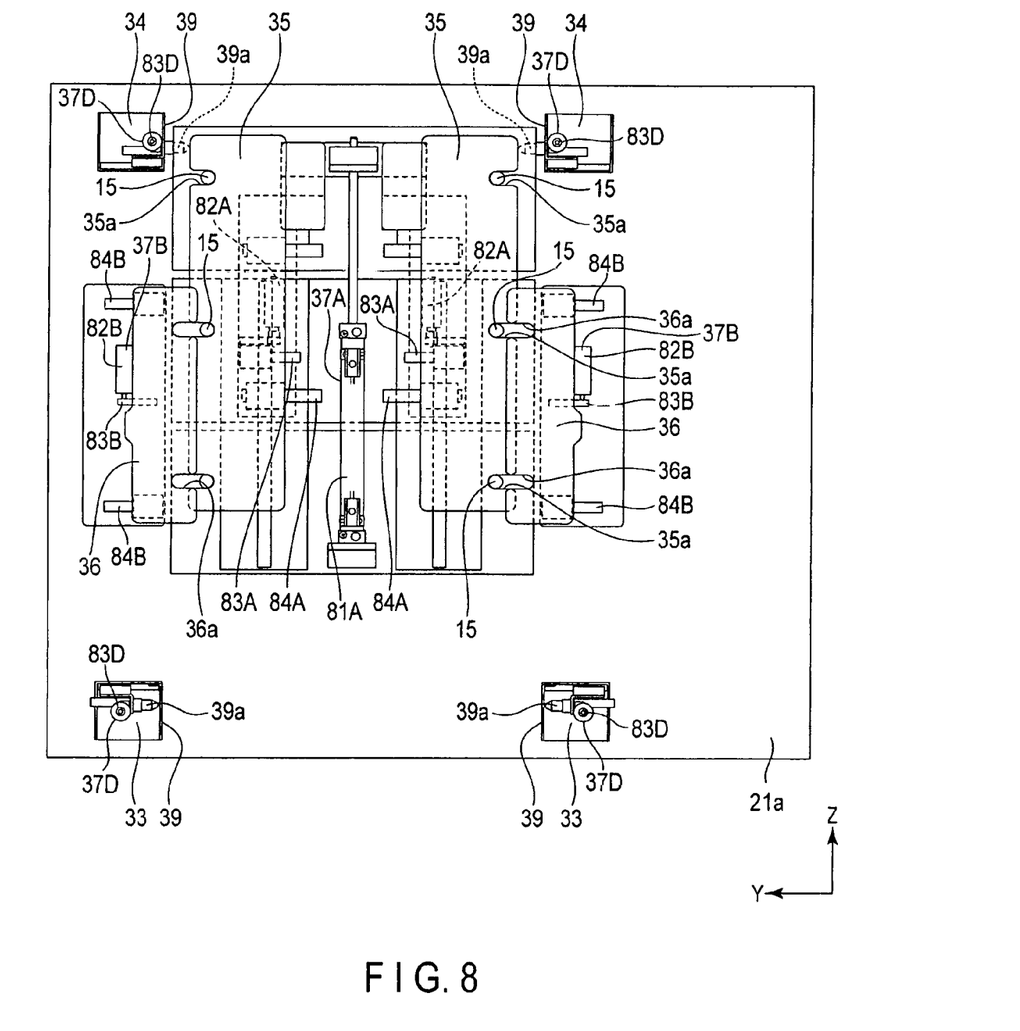
FIG. 8 is an explanatory diagram illustrating the movement mechanism of the centrifugal separation apparatus.

A centrifugal separation method according to the present embodiment will be described with reference to FIGS. 1 to 8. FIG. 7 illustrates a state where centrifugal separators 10 are arranged in the lower three stages and the lower slide mechanism 34 is in engagement with the centrifugal separators 10. FIG. 8 illustrates a state where centrifugal separators 10 are arranged in the upper three stages and the upper lower slide mechanism 33 is in engagement with the centrifugal separators 10. In the states illustrated in FIGS. 7 and 8, the centrifugal separators 10 are held by the movement frames 35, and the holding frames 36 are located at the release positions.

For centrifugal separation processing, the controller 70 performs (i) movement processing in which the movement mechanism 30 and transfer mechanisms 60 are driven to sequentially move the sample containers 18 or centrifugal separators 10, and (ii) centrifugal separation processing in which the rotators of the respective centrifugal separators 10 are rotated at predetermined timings for centrifugal separation of samples.

As the movement processing, the take-in processing of sample containers 18 by the transfer mechanism 60, the lowering processing by the lowering mechanism 32, the sliding processing by the lower slide mechanism 34, the elevating processing by the elevating mechanism 31, the take-out processing of sample containers 18 by the transfer mechanism 60 and the slide processing by the upper slide mechanism 33 are performed at predetermined timings as a series of operations. In other words, the operation of taking in the sample containers 18 from the conveyance line 50 to a centrifugal separator 10, the operation of taking out the sample containers 18 from the centrifugal separator 10 to the conveyance line 50 and the operation of moving the centrifugal separator 10, are sequentially performed for each of the centrifugal separators 10.

According to the present embodiment, sample containers 18 are taken by the transfer mechanism 60 from the pickup position P1 on the conveyance line 50 into the centrifugal separator 10 located in the take-in position P2 (i.e., the uppermost stage of the descending column) by way of the opening of the lid 22 on the top plate of the base 20. The lowering mechanism 32 moves each centrifugal separator 10 from the take-in position P2 to the lowermost position P5 of the descending column after passing through the second stage position P3 and the third stage position P4. The lower slide mechanism 34 moves each centrifugal separator 10 to the lowermost position P6 of the ascending column. Subsequently, the elevating mechanism 31 moves each centrifugal separator 10 to the uppermost take-out position P9 of the ascending column after passing through the second stage position P7 and the third stage position P8. Then, the take-out transfer mechanism 60 takes out each centrifugal separator 10 from the take-out position P9 to the setting position P10 on the conveyance line 50.

Take-out processing is executed for the centrifugal separators 10 that have been moved from the take-in position P2 to the take-out position P9. Thereafter, the centrifugal separators 10 are circulated such that they are returned to the take-in position.

According to the present embodiment, the controller 70 preforms different kinds of processing for the respective seven centrifugal separators 10. Let us assume that the state shown in FIG. 5 (in which the lowermost stage of the descending column is empty) is a reference state. In this reference state, the take-in processing is executed for the centrifugal separator 10A located at the take-in position P2. Simultaneous with this take-in processing, take-out processing is executed for the centrifugal separator 10G located at the take-out position P9. During the take-in processing and take-out processing, centrifugal separation processing is executed for the other centrifugal separators 10B-10F, in which the rotators 13 are rotated.

After centrifugal separator 10A is taken in, the three centrifugal separators 10A, 10B and 10C in the descending column are lowered, and centrifugal separator 10G is slid to the take-in position P2 which becomes empty as a result of the lowering processing. Subsequently, the centrifugal separators 10D, 10E and 10F in the ascending column are elevated. Since the lowermost position P6 of the ascending column becomes empty as a result of the elevating processing, centrifugal separator 10C is moved thereto from the lowermost position P3 of the descending column. As a result, the state of the apparatus returns to the reference state, thereby ending one-turn processing. By repeating this one-turn processing for centrifugal separators 10A, 10G, 10F, 10E, 10D, 10C and 10B in this order, the one-cycle processing ends, and the centrifugal separation processing is completed for the eighty-four buckets 14 of the seven centrifugal separators. By repeating this one-circulation processing, the moving processing and the centrifugal separation processing are executed for a plurality of centrifugal separators 10, and simultaneous with them the take-in processing and take-out processing are executed.

<Take-In Processing>

The controller 70 drives the take-in transfer mechanism 60 to take sample containers 18, which are to be processed, in the centrifugal separator 10 located in the take-in position P2. By way of example, a description will be given of the case where transfer processing executed in two stages, in each of which a half (six) of the twelve buckets 14 are taken. To be more specific, the belt conveyance mechanism 64 and the cylinder mechanisms 62 and 63 are driven to move the container hands 61 to the pickup position P1. The container hands 61 are moved down, and the sixth sample containers 18 linearly arranged in the pickup position P1 are held or clamped by container hands 61. The container hands 61 are raised again and moved to the take-in position P2. Subsequently, the container hands 61 are moved down, by which sample containers 18 are taken into a half of the annually arranged buckets 14. Then, the motor 12 is driven so that the rotator 13 is rotated by half the circumference and the remaining buckets 14 are arranged in the take-in position P2. By repeating the take-in processing, sample containers 18 are taken in the remaining buckets of half the circumference.

In the present embodiment, the pickup position P1 is linear on the conveyance line 50. In place of this, the opening/closing claws 61*a* may be arranged along a curved line in accordance with the arrangement of the buckets 14 by adjusting the moving distances of the container hands 61 in the Y direction. By so doing, the pickup position is changed from linear to arcuate, and take-in processing is enabled for such an arcuate position as well. In the manner mentioned above, twelve sample containers 18 are taken into one centrifugal separator 10.

<Lowering Processing>

For lowering processing, the processor 70 drives the lowering mechanism 32 in such a manner that the centrifugal separators for which take-in processing is executed are sequentially lowered to the lowermost stage. To be more specific, the movement frames 35 are advanced until they engage with the engagement projections 15 of the centrifugal separators 10, and with the holding frames 36 retreated, the movement frames 35 are lowered by the distance corresponding to one stage. After the centrifugal separator 10 is lowered by the one-stage distance, the holding frames 36 are advanced until they engage with the engagement projections 15, and with the movement frames 35 retreated, the movement frames 35 are elevated, by which the lowering mechanism 32 is returned to the initial position. In the manner described above, the lowering processing for one stage is completed. By repeating the above lowering processing, the centrifugal separators 10 are sequentially lowered by the one-stage distance while being kept held. The paired lowering mechanisms located at the front and rear positions are coupled by a coupling shaft 86 and operate in synchronism with each other.

<Lower Slide Processing>

For lower slide processing, the controller 70 drives the lower slide mechanism 34 to move a centrifugal separator 10 from the lowermost stage of the descending column to the lowermost stage of the ascending column. To be more specific, the lowermost casing 11 is kept held by advancing the engagement pins 39*a* and inserting them into the engagement holes. In this state, the slider 39 is moved in the X direction so that the casing 11 is moved from the descending column to the ascending column. The engagement pins 39*a* are then retreated to release the lowermost casing 11 from the held state, and the slider 39 is moved in the Y direction to the original position. A series of operations for the lower slide processing are repeatedly executed at predetermined timings. The paired lower slide mechanisms located at the front and rear are coupled by the coupling shaft 86 and operate in synchronism with each other.

<Elevating Processing>

For elevating processing, the controller 70 drives the elevating mechanism 31 to sequentially elevate the centrifugal separators 10 in the ascending column to the take-out position P9. To be more specific, the movement frames 35 are engaged with the engagement projections 15 of the centrifugal separators 10, and with the holding frames 36 retreated to the release position, the movement frames 35 are raised to elevate the centrifugal separators 10. After the centrifugal separators 10 are elevated by the one-stage distance, the holding frames 36 are advanced until they engage with the engagement projections 15, and with the movement frames 35 retreated, the movement frames 35 are lowered, by which the elevating mechanism 31 is returned to the initial state. By repeating the above elevating processing, the centrifugal separators 10 are sequentially elevated by the one-stage distance while being kept held. The paired elevating mechanisms located at the front and rear are coupled by the coupling shaft 86 and operate in synchronism with each other.

<Upper Slide Processing>

For upper slide processing, the controller 70 drives the upper slide mechanism 33 to move a centrifugal separator 10 from the take-out position P9 to the take-in position P2. To be more specific, the controller 70 keeps holding the uppermost casing 11 by advancing the engagement pins 39*a* and inserting them into the engagement holes. In this state, the slider 39 is moved in the X direction so that the casing 11 is moved from the ascending column to the descending column. The engagement pins 39*a* are then retreated to release the uppermost casing 11 from the held state, and the slider 39 is moved in the X direction to the original position. A series of operations for the upper slide processing are repeatedly executed at predetermined timings. The paired upper slide mechanisms 33 located at the front and rear are coupled by the coupling shaft 86 and operate in synchronism with each other.

<Centrifugal Separation Processing>

The controller 70 drives the motor 12 such that the rotators 13 of the centrifugal separators 10 for which the take-in processing has been executed but the take-out processing has not yet been executed are rotated at predetermined timings. The timings are determined to enable centrifugal separation processing to be executed in parallel for the respective centrifugal separators 10. According to the present embodiment, when the take-in processing has been completed for the centrifugal separator 10 located at the take-in position P2, the motor 12 is driven to start centrifugal separation. The centrifugal separation processing is kept executed for a predetermined time until the centrifugal separator 10 is moved to the take-out position P9 by the movement processing. When the centrifugal separator 10 reaches the take-out position P9, the rotator 13 is stopped, and the sample containers 18 are sequentially taken out and returned to the processing line.

The centrifugal separation apparatus of the present embodiment advantageous in the following points. Since a plurality of centrifugal separators 10 are sequentially circulated along route Pa inside the base 20, a large number of sample containers 18 can be received in the base 20 and subjected to centrifugal separation processing. The processing efficiency can be enhanced, accordingly. Let us consider the case where a large number of sample containers 18 (e.g., forty sample containers 18) are taken in, centrifugal separation processing is executed after all sample containers 18 are taken in, and the sample containers 18 are taken out after the centrifugal separation processing is executed. In this case, the centrifugal separation processing cannot be performed when the sample containers 18 are being taken in or taken out, and the time loss is considerable. In contrast, the centrifugal separation apparatus 1 of the above embodiment enables centrifugal separation processing to be executed for sample containers 18 when the take-in operation or take-out operation is being executed for the other sample containers 18. Accordingly, the wait time can be shortened, and the time loss can be reduced.

In addition, the centrifugal separators 10 are arranged in the base 20 in stages and columns. This structure helps reduce the installation space.

The present invention is not limited to the above-described embodiment, and can be modified in various manners in practice without departing from the gist of the invention.

For example, each of the driving mechanisms 37A to 37D is not necessarily a driving mechanism comprising a rotary motor and a driving force transmission mechanism. In place of such a driving mechanism, a cylinder mechanism or a variety of other types of driving mechanism may be employed. In addition, the cylinder mechanisms employed in the above embodiment may be replaced with a rotary motor and a driving force transmission mechanism, or with another type of driving mechanism. The driving force transmission mechanism is not limited to a pinion-and-rack type but may be a screw type or another type of transmission mechanism. Likewise, the screw-type driving force transmission mechanism of the aforesaid embodiment may be replaced with a pinion-and-rack type or another type of transmission mechanism.

Some of the structural elements of the above-mentioned embodiment may be omitted, and the shape and/or structure of each structural element may be changed. Furthermore, various inventions can be made by properly combining the structure elements disclosed in the above embodiment.

The present invention is not limited to the above-described embodiments. In practice, various modifications may be made without departing from the spirit of the invention. Further, various inventions may be made by suitably combining a plurality of components described in connection with the foregoing embodiment. For example, some of the components according to the foregoing embodiment may be omitted. Furthermore, components according to different embodiments may be combined as required.

What is claimed is:

1. A centrifugal separation apparatus comprising:
a plurality of centrifugal separators each comprising a rotator which supports a plurality of sample containers containing a sample therein;
a base in which the centrifugal separators are arranged in columns and stages and a route is defined in the base, the centrifugal separators being movable inside the base;
a movement mechanism that sequentially move the centrifugal separators along the route in the base; and
a controller which executes movement processing in which the centrifugal separators are sequentially moved along the route in the base and centrifugal separation processing in which the rotator is rotated for centrifugal separation processing of the sample, wherein
the route includes a descending column, an ascending column, a take-in position located in an uppermost stage of the descending column, and a take-out position located in an uppermost stage of the ascending column, further comprising:
a take-in transfer mechanism which transfers the sample containers to be processed to the centrifugal separator located at the take-in position;
a take-out transfer mechanism which transfers the sample containers from the centrifugal separators located at the take-out position,
wherein the movement mechanism includes an elevating mechanism which sequentially elevates the centrifugal separators in the ascending column, a lowering mechanism which sequentially lowers the centrifugal separators in the descending column, a slide mechanism which slides a centrifugal separator between the ascending column and the descending column,
the controller repeatedly executes the movement processing, including take-in processing in which the take-in transfer mechanism takes in the sample containers to be processed into the centrifugal separator located at the take-in position; lowering processing in which the lowering mechanism sequentially lowers the taken-in centrifugal separators to a lowermost stage of the descending column; lower slide processing in which the slide mechanism moves a centrifugal separator from a lowermost stage of the descending column to a lowermost stage of the ascending column; an elevating processing in which the elevating mechanism sequentially elevates the centrifugal separators in the ascending column to the take-out position; take-out processing in which the take-out transfer mechanism takes out the sample containers from the centrifugal separator located at the take-out position; and upper slide processing in which the slide mechanism moves the centrifugal separator subjected to the take-out processing to the take-in position again, and the controller also executes the centrifugal separation processing in which the rotator is rotated, for the centrifugal separators for which the take-in processing is executed and the take-out processing is not executed.

2. The centrifugal separation apparatus according to claim 1, wherein each of the elevating mechanism and the lowering mechanism comprises a holding frame which holds the centrifugal separators and a movement frame which elevates the centrifugal separators in a state where the centrifugal separators are held, and
the slide mechanism comprises a slider which is moved back and forth between the ascending column and the descending column in a state where the slider is in engagement with one of the centrifugal separators.

3. A centrifugal separation method for a route comprising a descending column and an ascending column, in each column of which a plurality of centrifugal separators are arranged, each of the centrifugal separators comprising a rotator configured to support a plurality of sample containers containing a sample therein, the route also comprising a take-in position located in an uppermost stage of the descending column and a take-out position located in an uppermost stage of the ascending column,
said centrifugal separation method comprising:
executing movement processing including:
taking sample containers, which are to be processed, in a centrifugal separator located at the take-in position;
lowering the centrifugal separator, in which the sample containers are taken, to a lowermost stage of the descending column;
moving the centrifugal separator from the lowermost stage of the descending column to a lowermost stage of the ascending column;
sequentially elevating centrifugal separators in the ascending column to the take-out position;

taking the sample containers out from the centrifugal separator located at the take-out position; and moving the centrifugal separator, from which the sample containers are taken out, to the take-in position, and simultaneous with the movement processing, rotating the rotator of each of the centrifugal separators for which the take-in processing has been executed and the take-out processing has not yet been executed.

* * * * *